United States Patent [19]

Nalewajek

[11] 4,438,078

[45] Mar. 20, 1984

[54] RECOVERY OF GADOLINIUM AND GALLIUM OXIDES

[75] Inventor: David Nalewajek, West Seneca, N.Y.

[73] Assignee: Allied Corporation, Morris Township, Morris County, N.J.

[21] Appl. No.: 451,296

[22] Filed: Dec. 20, 1982

[51] Int. Cl.$^3$ .................. C01G 15/00; C01F 17/00
[52] U.S. Cl. .................. 423/21.5; 423/21.1; 423/112; 423/114; 423/122; 423/127; 423/132
[58] Field of Search .................. 423/21.1, 21.5, 112, 423/114, 122, 127, 132

[56] References Cited

U.S. PATENT DOCUMENTS

| | | |
|---|---|---|
| 3,144,304 | 8/1964 | Nagumo et al. |
| 3,506,585 | 4/1970 | Otsuka et al. .................. 423/21.1 |
| 4,198,231 | 4/1980 | Gusset. |
| 4,369,166 | 1/1983 | Nalewajek .................. 423/112 |
| 4,375,453 | 3/1983 | Nalewajek et al. .................. 423/21.1 |

FOREIGN PATENT DOCUMENTS

| | | | |
|---|---|---|---|
| 21990 | 1/1981 | European Pat. Off. | .......... 423/112 |
| 54461 | 6/1982 | European Pat. Off. | .......... 423/112 |

OTHER PUBLICATIONS

Chem. Abstr., vol. 83, 184046n, Y. P. Kudryavskii et al.
Chem. Abstr., vol. 84, 20647d, A. V. Plyusnin et al.
Chem. Abstr., vol. 85, 136608s (1976), M. Chakravorty et al.
Schultz et al., "Chem. Absts.", vol. 85, 1976, #66231n.
Chem. Abstr., vol. 65, 11384f (1966), Otto Klug et al.
Chem. Abstr., vol. 82, 160637j (1975), Wodkiewicz et al.
Chem. Abstr., vol. 82, 148933v (1975), R. Dybczynski et al.

*Primary Examiner*—Herbert T. Carter
*Attorney, Agent, or Firm*—Arthur J. Plantamura; Jay P. Friedenson; Richard C. Stewart, II

[57] ABSTRACT

A process is described whereby gadolinium and gallium containing by-products can be reprocessed to yield the oxides of these elements in sufficient purity to be re-used in the process for manufacturing $Gd_3Ga_5O_{12}$ (GGG) single crystal boules thereby improving the economics of production of GGG wafers significantly. The gadolinium and gallium oxides are recovered and separated from transition metal impurities introduced during fabrication of GGG wafers by precipitating the gadolinium as oxalate which is thereafter pyrolyzed to gadolinium oxide and eluting the gallium containing filtrate over an ion exchange resin and precipitating therefrom as an oxalate the gallium present. The gallium precipitate is also pyrolyzed to the gallium oxide. The process can be extended to include purification and re-use of by-products generated in other grinding and polishing operations which may result in the recycling of the order of 80% of the generated by-products.

7 Claims, No Drawings

RECOVERY OF GADOLINIUM AND GALLIUM OXIDES

DESCRIPTION

This invention relates to a method for recovering the essential elements from manufacturing by-products and more particularly to the recovery of gadolinium and gallium by-products generated during fabrication of gadolinium gallium garnet (GGG) wafers in a purity suitable to be recycled in the process. In particular, the GGG by-products are transformed to compounds which can be conveniently separated from each other and from transition metal impurities (based on solubilities) and converted to high purity oxides.

BACKGROUND OF THE INVENTION

In recent years, the electronics industry has invested substantially in time and money in bubble device technology which is used in advanced computer hardware. The attraction for this investment has centered on the expectation of a rapidly expanding bubble memory market. These devices serve to span the gap between expensive semiconductors and the mechanically sensitive magnetic disks and tapes used in computer technology.

The substrate wafer material for these bubble memory devices is composed of a stoichiometric composition of gadolinium-gallium oxides, $Gd_3Ga_5O_{12}$, commonly referred to as gadolinium-gallium garnet or GGG. Current fabrication techniques for these wafers result in the generation of the order of 80% GGG by-products that are based on relatively expensive starting materials. A method for the recovery and separation of high purity oxides from the GGG by-products so that the material could be re-used in the process in a practical manner would aid significantly the economics of production of GGG wafers.

While the problem of by-product recovery and purification has existed for a number of years in the industry, and attempts to recover by-products have been reported such as the means that involves digesting the scrap material, precipitating the gadolinium and electrolytically depositing the gallium as described in U.S. Pat. No. 4,198,231, the search continues for a more satisfactory, practical way for efficiently recovering the by-product in an economically attractive manner for an industrial size facility. In view of the substantial economies involved, a need exists for improved means to recover gadolinium and gallium from the GGG wafer fabrication by-products.

SUMMARY OF THE INVENTION

The precipitation and isolation of gadolinium from gallium and transition metal impurities is based on the insolubility of gadolinium oxalate, $Gd_2(C_2O_4)_3$, at low pH (about 0.5–1). The purification and isolation of gallium from the transition metal impurities is based on the adsorption-desorption properties of complex metal ions formed in various normal strength acid solutions. Whereas gallium forms species of the type $MCl_4^-$, many of the transition metal impurities present do not. This fact allows gallium to be selectively desorbed from various anion exchange resins.

In accordance with the present invention, gadolinium and gallium oxide by-products generated during fabrication of GGG wafers can be separated and recovered in an acceptable purity by transforming the GGG waste materials into compounds which can conveniently be separated from each other as well as from transition metal impurities based on the solubility or absorption properties of the metals in an acidic solution. The intermediate compounds thus produced are easily converted to high purity oxides.

The by-product material, consisting of $Gd_3Ga_5O_{12}$, to be reclaimed is separated from lubricating oil by vacuum filtration, thermally treated to remove any remaining organic substrate contaminants which adhere to the particles, is dissolved in mineral acids and, after digestion to ensure dissolution, the solution is filtered to remove insoluble particles. The gadolinium and gallium salts are then precipitated from the particle free solution as oxalates or ammonium oxalate salts and converted to the oxides.

After pretreatment and dissolution in mineral acid of the gadolinium and gallium by-products as described above, the filtrate is heated to 80° C. and solid oxalic acid is added to precipitate gadolinium oxalate, $Gd_2(C_2O_4)_3$. The precipitate, which forms immediately, is separated from gallium and transition metal impurities by conventional methods, by either vacuum filtration or centrifugation. The cake of gadolinium oxalate, thus obtained, may be slurried in a water solution containing 2% by weight of oxalic acid to remove trace adhering gallium solution. The yield of gadolinium oxalate is of the order of >95%. Direct pyrolysis of this oxalate at 850°–950° C. results in its conversion to gadolinium oxide, $Gd_2O_3$, in >95% yield and >99.99% purity.

The combined filtrates from the above process are eluted on a column comprised of a suitable ion exchange resin such as the commercially available styrene-divinyl-benzene copolymers containing quaternary ammonium functionality. Elution with hydrochloric acid results in the removal of most of the transition metals. The fraction containing the gallium is eluted and treated with oxalic acid or compound generating oxalic acid ion, e.g. ammonium oxalate. After the pH of this solution is adjusted to 8.5, the precipitation of ammonium gallium oxalate, $NH_4Ga(C_2O_4)_2$, and gallium hydroxide, $Ga(OH)_3$, is complete. Filtration by conventional techniques followed by pyrolysis at 850°–950° C., results in the isolation of gallium oxide, $Ga_2O_3$, in the order of 80% yield and 99.99% purity.

DETAILED DESCRIPTION OF THE INVENTION

While the process of the invention is described specifically with reference to the residue or "saw kerf", derived from slicing the crystal boules into wafers, the invention can be extended to include the purification of by-products generated in other manufacturing stages. Minor revisions in the pre-treatment of the by-products may be necessary. These can include: (a) grinding (ball milling) of boule heels or boule ends before dissolution; (b) cracking of these same boule entities by thermal shock treatment before dissolution or (c) washing the by-products generated during polishing steps with a liquid organic, e.g., a chlorofluorocarbon solvent, to eliminate lubricating oils.

In the reprocessing of saw kerf, the material to be reclaimed is separated from lubricating oil by vacuum filtration and then thermally treated at about 700° C. to remove any remaining organic substrate which adheres to the particles. This treated material, which consists of gadolinium-gallium oxide, $Gd_3Ga_5O_{12}$, and transition metal impurities identified as magnesium, nickel, zirconium, aluminum, iron and silicon, as well as diamond dust and aluminum oxide particles, is dissolved in a suitable mineral acid which does not form compositions that react adversely with the ion exchange resin, preferably hydrochloric acid. Nitric acid is to be avoided because it may form an explosive composition or may otherwise interfere with the ion exchange process. After digesting for a suitable period, e.g., about 3 hours, to ensure maximum dissolution, the solution is filtered to remove insoluble particles. These particles consist mainly of diamond dust, aluminum oxide and $Gd_3Ga_5O_{12}$ of particle size $>250$ $\mu$m. If substantial amounts of $Gd_3Ga_5O_{12}$ are collected on the filter, they can be ground to a smaller size and treated again with mineral acid. However, accumulation of material on the filter is not usually observed when the by-product being processed in accordance with the invention is saw kerf. The gadolinium and gallium salts are then precipitated from the particle free solution as oxalates or ammonium oxalate salts as described below.

The precipitation and isolation of gadolinium from gallium and transition metal impurities is based on the insolubility of gadolinium oxalate, $Gd_2(C_2O_4)_3$, at low pH (0.5–1). The purification and isolation of gallium from the transition metal impurities is based on the adsorption-desorption properties of complex metal ions formed in various normal strength acid solutions. Whereas gallium forms species of the type $MCl_4^-$, many of the transition metal impurities present do not. This fact allows gallium to be selectively desorbed from various anion exchange resins.

In effecting the separation of the gadolinium and gallium from the GGG by-product, after pretreating the saw kerf as described above, the filtrate is heated to 80° C. and solid oxalic acid, or compound generating oxalic acid ion, is added to precipitate gadolinium oxalate, $Gd_2(C_2O_4)_3$. Examples of compounds generating oxalic acid ion include: ammonium oxalate, potassium oxalate, sodium oxalate and the like. The precipitate, a white microcrystalline material, begins to form immediately and is separated from gallium and transition metal impurities in a suitable conventional manner, e.g., by vacuum filtration or centrifugation. The cake of gadolinium oxalate, thus obtained, may be cleansed of adhering gallium containing filtrate by slurrying with a water solution containing 2% by weight of oxalic acid. The yield of gadolinium oxalate obtainable is consistently >95%. Direct pyrolysis of this oxalate at 850°–950° C. results in its conversion to gadolinium oxide, $Gd_2O_3$, in >95% yield and >99.99% purity.

The combined filtrates from the above process are eluted on a column comprised of a suitable ion exchange resin containing a quaternary ammonium functionality and exhibiting resistance to chemical degradation. The resin bead structure is based on a styrene-divinylbenzene copolymer such as the anion exchange resin available commercially under the brand name Amberlite IRA-400 from Rohm & Haas Co. Ion exchange resins are characterized by active groups that give the resin the property of combining with or exchanging ions between the resin and the solution. Elution with various strengths of hydrochloric acid results in the removal of most of the transition metals. This is accomplished in the range of 12-6 N acid. When the acid concentration is finally adjusted to about 1 N, the fraction containing the gallium is eluted and subsequently treated with ammonium oxalate. After the pH of this solution is adjusted to 8.5, the precipitation of ammonium gallium oxalate, $NH_4Ga(C_2O_4)_2$, and gallium hydroxide, $Ga(OH)_3$, is complete. Filtration by conventional techniques followed by pyrolysis at 850°–950° C., results in the isolation of gallium oxide, $Ga_2O_3$, in the order of 80% yield and 99.99% purity.

The several features and advantages of the invention will be apparent in greater detail by the following examples. It will be understood, however, that although these examples may describe in detail certain preferred operation conditions of the invention, they are given primarily for purposes of illustration and the invention in its broad aspects is not limited thereto.

EXAMPLE 1

Dried saw kerf, recovered from gadolinium-gallium-garnet, $Gd_3Ga_5O_{12}$, of composition 54% gadolinium oxide and 46% gallium oxide, was pyrolyzed at 700° C. for 3 hours to decompose volatile impurities. 59 g of the pyrolyzed material, with a particle size $\leq 250$ $\mu$m, was refluxed for 3 hours in 150 mL of 37% hydrochloric acid. The solution which contained gadolinium and gallium chlorides in addition to the transition metal chlorides was filtered to remove 0.5 g of insoluble particles. This particle free solution was heated to 80° C. then treated with 100 g of solid oxalic acid. The precipitation of gadolinium oxalate as a white microcrystalline solid began immediately. The mixture was stirred for 2 hours at 80° C. followed by 6 hours at ambient temperature and filtered. The filter cake was slurried in 50 mL of a water solution containing 2% by weight oxalic acid. Filtration and pyrolysis resulted in the isolation of 31 g (97%) of gadolinium oxide, $Gd_2O_3$. Purity based on trace metal analysis was 99.995%.

A column of dimensions 6 cm $\times$ 120 cm containing 1300 g of Amberlite IRA-400 anion exchange resin (resulting in a final bed depth of 80 cm) was activated with 12 N hydrochloric acid (Flow rate=150 mL/h). The filtrate from above was adsorbed on the column and the transition metals eluted with 7 L of 6 N hydrochloric acid. At this stage, virtually all of the metal impurities were removed with the exception of iron (III) which trailed on the column. The eluting acid concentration was adjusted to 1 N and the gallium collected in 1.5 L of the eluant. 85 g of ammonium oxalate was added to this solution and the pH adjusted to 8.5. The precipitate of ammonium gallium oxalate and gallium hydroxide which formed immediately was stirred for 4 hours at ambient temperature and filtered. The filter cake was washed once with 250 mL of a water solution to which ammoniumn hydroxide had been added to adjust the final pH to 7.2. Pyrolysis of this gallium residue resulted in the isolation of 22 g (82%) of gallium oxide, $Ga_2O_3$. Purity based on trace metal analysis was 99.990%. The major contaminant was iron (III).

EXAMPLE 2

59 g of saw kerf was treated as described above. The gadolinium was removed as discussed in Example (1). The resin column was prepared as in Example (1) except that 10% ascorbic acid was added. Transition metals were removed with 6 N acid. Elution with 1 N hydrochloric acid resulted in the isolation of 21 g (80%) of gallium oxide. Purity based on trace metal analysis was 99.994%. The ascorbic acid was effective in reducing iron (III) to iron (II) which did not adsorb strongly to the resin.

As hereinabove described, it is seen that the present invention is characterized by the following steps or observations:

(1) Dissolution of the gadolinium and gallium oxide by-product in hydrochloric acid.
(2) Precipitation of gadolinium oxalate at a pH range of about 1.
(3) Pyrolysis of gadolinium oxalate to yield high purity oxide.
(4) Use of an anion exchange resin to remove transition metal impurities.
(5) Elution of filtrate obtained in step 2 with 6 N HCl to remove metal impurities.
(6) Elution of gallium with HCl.
(7) Addition of ammonium oxalate to eluant in step (6).
(8) pH adjustment of solution from step (7) to a pH of about 8.5.
(9) Filtration of precipitate formed in step (8) consisting of ammonium gallium oxalate and gallium hydroxide.
(10) Pyrolysis of precipitate obtained in step (9) to yield high purity $Ga_2O_3$, i.e., of the order of 99.990% purity.
(11) Ascorbic acid may be added to the ion exchange column to reduce Iron (III) to Iron (II). For applications, use of ascorbic acid gives preferred results.
(12) Elution of material as described in steps (5) and (6).
(13) Work up of eluant as described in steps (7) to (9).
(14) Pyrolysis to yield high purity $Ga_2O_3$ (99.994%).
(15) Low levels of cross contamination of the two oxides (<10 ppm).

It will be understood that variations may be made in the several conditions and ranges disclosed and that these disclosed limitations, provided in order to more particularly describe the invention, should not be regarded as limitations except as set forth in the claims which follow:

What is claimed is:

1. A method for recovering gadolinium and gallium oxides from by-product material which contains both of these oxides and various impurities comprising the steps of:

(a) dissolving the gadolinium and gallium oxide in a strong mineral acid that does not yield compositions which react adversely with an ion exchange resin used in separation of the gallium oxide, (b) filtering the solution of (a), isolating the filtrate, adding a compound generating oxalic acid ion and precipitating the gadolinium as oxalate from said filtrate, (c) separating, washing and drying the precipitated gadolinium oxalate, (d) converting the gadolinium oxalate salt from step (c) by calcining the recovered gadolinium oxalate to yield gadolinium oxide, (e) contacting the filtrate from step (b) with an ion exchange resin containing a quaternary ammonium functionality, eluting the resin with an acid having a concentration in the range 6–12 N and thereafter eluting the resin with an acid having a concentration of about 1 N to elute the gallium fraction, (f) reacting the filtrate containing the gallium fraction eluted in step (e) with a compound generating oxalic acid ion and precipitating the gallium oxalate by basifying the acidic filtrate solution, (g) washing and drying the gallium oxalate salt and gallium hydroxide which precipitates from step (f), and (h) calcining the precipitate of step (g) to form gallium oxide.

2. The method of claim 1 wherein the gadolinium and gallium oxide by-product in step (a) is dissolved in hydrochloric acid.

3. The method of claim 1 wherein the gadolinium and gallium oxide dissolved in step (a) is preheated to remove organic impurities.

4. The method of claim 1 wherein the filtrate in step (f) is reacted with ammonium oxalate.

5. The method of claim 1 wherein the ion exchange resin in step (e) is a styrene-divinylbenzene copolymer with a trimethyl ammonium functionality as the active group.

6. The method of claim 5 wherein the ion exchange step is conducted in an ion exchange resin bed having a depth of at least 50 cm.

7. The method of claim 6 wherein ascorbic acid is added to the ion exchange column to reduce the valence of any iron contaminant present.

* * * * *

UNITED STATES PATENT AND TRADEMARK OFFICE
CERTIFICATE OF CORRECTION

PATENT NO. : 4,438,078
DATED : March 20, 1984
INVENTOR(S) : David Nalewajek

It is certified that error appears in the above–identified patent and that said Letters Patent are hereby corrected as shown below:

Col. 4, line 20, "$\leqq 250 \ \mu m$" should read -- $\leq 250 \ \mu m$ --

Signed and Sealed this

Thirtieth Day of April 1985

[SEAL]

*Attest:*

DONALD J. QUIGG

*Attesting Officer*     *Acting Commissioner of Patents and Trademarks*